United States Patent
Stinson et al.

(10) Patent No.: US 8,903,892 B2
(45) Date of Patent: Dec. 2, 2014

(54) SOFTWARE BASED SYSTEM FOR CONTROL OF DEVICES

(75) Inventors: Dave Stinson, Uxbridge (CA); Gary Schissler, Port Perry (CA)

(73) Assignee: Oasys Healthcare Corporation, Uxbridge (CA)

( * ) Notice: Subject to any disclaimer, the term of this patent is extended or adjusted under 35 U.S.C. 154(b) by 273 days.

(21) Appl. No.: 13/111,646

(22) Filed: May 19, 2011

(65) Prior Publication Data

US 2012/0296957 A1  Nov. 22, 2012

(51) Int. Cl.
*G06F 15/16* (2006.01)
*G06F 15/177* (2006.01)
*G06F 19/00* (2011.01)

(52) U.S. Cl.
CPC .................. *G06F 19/327* (2013.01)
USPC ............................ 709/203; 709/219; 709/221

(58) Field of Classification Search
USPC .......................................... 348/145, 153–161
See application file for complete search history.

(56) References Cited

U.S. PATENT DOCUMENTS

| | | | |
|---|---|---|---|
| 6,646,541 B1 | 11/2003 | Wang et al. | 340/3.54 |
| 7,833,219 B2 | 11/2010 | Tashiro et al. | 606/1 |
| 2005/0128184 A1 | 6/2005 | McGreevy | 345/156 |
| 2005/0284491 A1 | 12/2005 | Tashiro | 128/897 |
| 2007/0250191 A1* | 10/2007 | Rourke et al. | 700/90 |
| 2007/0282748 A1* | 12/2007 | Saint Clair et al. | 705/51 |
| 2009/0144010 A1* | 6/2009 | Witter et al. | 702/115 |
| 2009/0259972 A1* | 10/2009 | Kodosky et al. | 715/810 |
| 2009/0281393 A1* | 11/2009 | Smith | 600/301 |
| 2011/0167250 A1* | 7/2011 | Dicks et al. | 713/2 |
| 2011/0238434 A1* | 9/2011 | Froehlich | 705/2 |
| 2012/0053423 A1* | 3/2012 | Kenalty et al. | 600/300 |
| 2012/0117588 A1* | 5/2012 | McCoy et al. | 725/28 |

* cited by examiner

*Primary Examiner* — Ayaz Sheikh
*Assistant Examiner* — Mariela Vidal Carpio
(74) *Attorney, Agent, or Firm* — Jonathan M. D'Silva; MacDonald, Illig, Jones & Britton LLP

(57) ABSTRACT

What is presented is a medical environment control system includes a plurality of audio/video devices, a server and a client system. Each one of the plurality of audio/video devices receives or sends an audio/video signal. The server is connected to each one of the plurality of audio/video devices and is configured to controllably receive and send audio/video signals to and from the plurality of audio/video devices. The client system is interoperable with the server and with a user of the client system through a user interface. At least one medical device is also connected to communicate with the server. The user can control the plurality of audio/video devices through the client system and the server, and receive the one audio/video signal outputted from any one of the plurality of audio/video devices and the at least one medical device at the client system.

26 Claims, 14 Drawing Sheets

SOFTWARE BASED SYSTEM FOR CONTROL OF DEVICES

FIELD OF THE INVENTION

The invention relates to a system for control of devices. More particularly, the invention relates to a software based system for control of networked devices in a medical environment.

BACKGROUND

General purpose control systems for devices are commercially available from multiple sources, such as from Crestron Electronics, Inc. of Rockleigh, N.J. Such systems typically have a main or "master" controller that may be independent or integrated with a device such as Adagio Audio that serves as the control processor. The control processor is loaded with code using logic symbols defining how each device will be used. Devices may be placed into the system and specify which control port those devices are connected to and default options for that device. The devices are controlled by the central controller via their communication interfaces Conventional general purpose control systems may be adapted for a variety of environments, such as educational and medical environments. A modern medical environment, particularly an operating room or other surgical environment, may have multiple different devices, including environmental, audio-visual (AV) devices and particular medical devices that are desired without any consideration of the environment control system. While some devices such as lighting device might be considered standard, in some medical environments there may be an uncompromising insistence on using particular medical devices, and a control system has to be able to adapt to such medical devices.

Environmental devices include devices such as room lights and room cameras. AV devices include devices such as displays and display panels, CD (Compact Disc) players, DVD (Digital Versatile Disc) recorders, VTRs (Video Tape Recorder) and reference image storage servers. Medical devices include devices such as ultrasound equipment, laparoscopes, x-ray machines, laser scalpels, surgical lights, medical navigation devices and endoscopes. Some medical devices, such as endoscopes, provide video or image signals. The devices in a medical environment can be interconnected in a network and have the same communication interface (or at least operate according to the same communication protocol). Examples of such medical environments are discussed in U.S. Patent Application Publication Nos. 2005/0128184 and 2005/0284491.

However, unlike other environments, there are several problems associated with the control system for devices in a medical environment. Since the medical procedures cannot be adversely affected by a device or system failure, the network and control system tends to be limited in functionality and convenience when compared to other environments. Medical environments are not the same and each one will differ in the configuration of devices, and configuration of the control system for an individual unique medical environment presents special considerations. Even the same medical environment can be different over time as medical devices or other devices are removed or added to the environment.

Conventionally, the control system for an individual medical environment is unique and the software utilized in the control system is custom built and installed. When a device is added to the environment, the custom built software has to be recompiled. These limitations implicate practical limitations on the control systems for medical environments. The systems cannot be set up by medical personnel and must be set up by a person having knowledge of the programming language.

Some control systems have associated software programs that enable some steps in the automation of controlled devices to be automatically generated. For example, once a device has been dragged into the configuration in Crestron's Systembuilder programming platform, the programmer can use automatically generated templates or can manually create page design layouts with VTPro e (Crestron's touch panel design interface). After the code has been complied and loaded onto the "control system" it cannot be retrieved to edit or change and can only be changed by a person with a copy of the original program. They cannot be viewed or changed by the end user.

In a Crestron system, only an external PC loaded with either SIMPL Windows software or the Systembuilder program can change the way the system functions and, as mentioned above, the program loaded onto the system would be required. The end user may change only items such as saving pre-sets or timers. If a piece of equipment needs to be changed a certified developer would be required to make changes to the program, recompile and upload to the control processor. This also applies to the layout and naming of buttons on Touch Panels which need to be modified via Systembuilder or VTPro e. In a Creston environment there is no device native to the system that can by an end user edit any part of the operation of the program or the visual aesthetics of any touch panel connected to the system.

Both Systembuilder and SIMPL Windows rely on an external program (VTPro e) to create Touch Panel pages and then use digital links (joins) in order to associate the program to the Touch Panel buttons. Systembuilder is capable of creating some of these links automatically however again this cannot be accessed through the control system itself or by an end user. The Programmer can select a theme for the Touch Panels which will define colours and button attributes and this theme and all pages for control need to be uploaded to each Touch Panel or Panel Processor. Again once this has been loaded it cannot be changed by the user and cannot be extracted from the system.

BRIEF SUMMARY OF THE PREFERRED EMBODIMENTS

The preferred embodiments of the invention include a control system with audio/video devices, a server and a client system. Each one of the audio/video devices receives or sends an audio/video signal. The server is connected to each one of the audio/video devices and is configured to controllably receive and send audio/video signals to and from the audio/video devices. The client system is interoperable with the server and with a user of the client system through a user interface. At least one medical device may also be connected to communicate with the server. The user can control the audio/video devices through the client system and the server, and receive the audio/video signal outputted from any one of the audio/video devices and the medical device at the client system.

BRIEF DESCRIPTION OF THE DRAWINGS

For a more complete understanding and appreciation of the preferred embodiments of the invention, and its many advantages, reference will be made to the following detailed description of the preferred embodiments taken in conjunction with the accompanying drawings.

DETAILED DESCRIPTION OF THE PREFERRED EMBODIMENTS

Several preferred embodiments of the invention will now be described with reference to the attached drawings. It will be understood that the preferred embodiments are exemplary, non-limiting, embodiments which can be varied in some respects and still be within the scope of the invention. For example, although the preferred embodiments utilize a specific distributed client server model as discussed herein, different models can be utilized as well. And although a specific portable configuration file is defined in the preferred embodiments, different configuration files can be utilized as well.

The embodiments of the invention may take form in various components and arrangements of components, and in various steps and arrangements of steps. The drawings are only for the purposes of illustrating a preferred embodiment and are not to be construed as limiting the invention. Portions of the preferred embodiments can generally be interchanged with corresponding substitute portions whether currently existing or hereafter developed without deviating from the invention.

Figure 1:
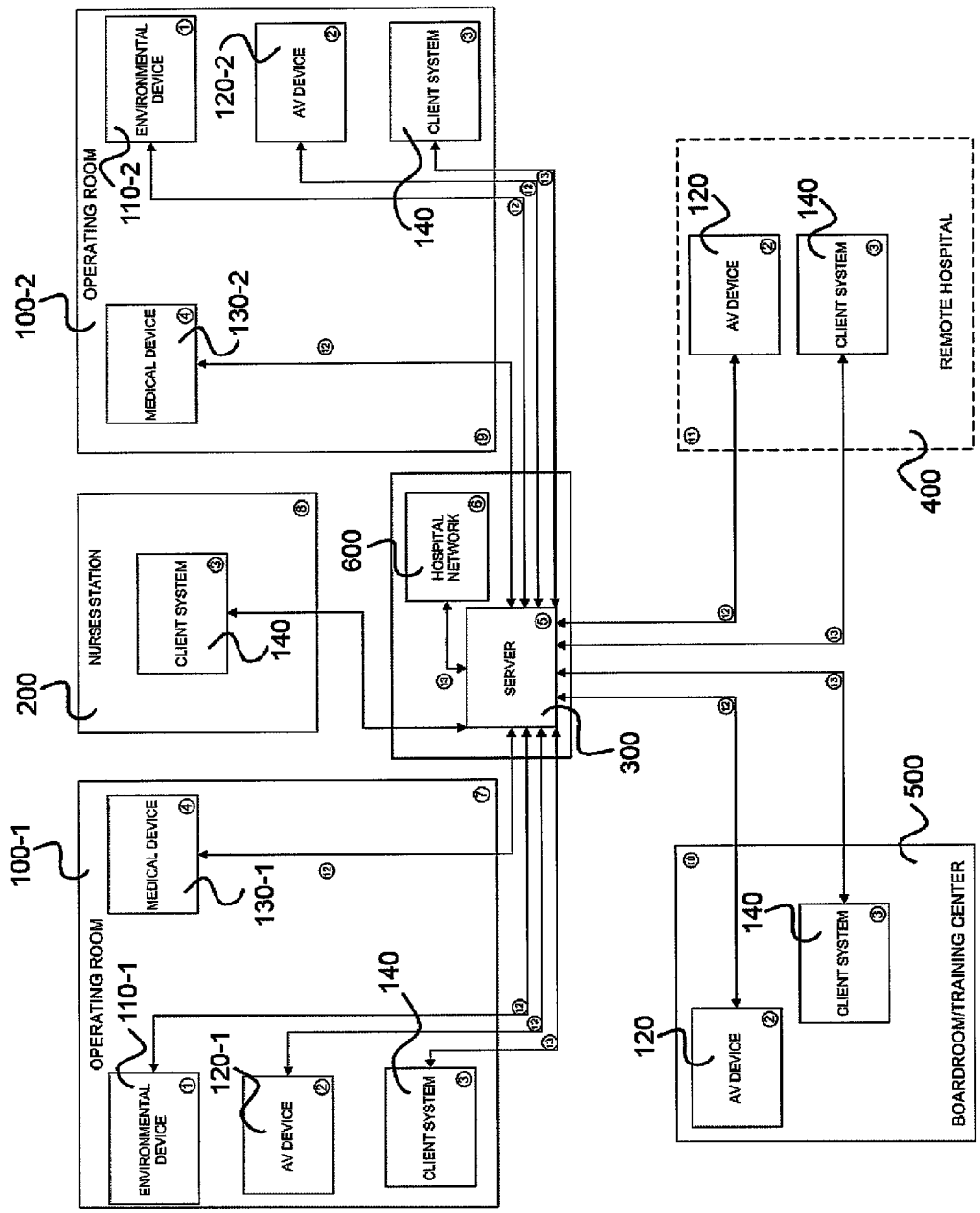
FIG. 1 is a block diagram of a control system for devices in a surgical environment according to a preferred embodiment of the invention.

An exemplary surgical environment is shown in FIG. 1. However, the preferred embodiments can also be utilized in other medical environments, such as an emergency or trauma room, an intensive care unit, a patient or observation room, or a diagnostic imaging environment such as ultrasound, X-ray or magnetic resonance imaging (MRI). It includes two operating rooms 100-1 to 100-2, a nurse's station 200 and a server 300. Although two operating rooms and one nurse's station are shown in the example of FIG. 1, there may be a different number of operating rooms or nurse's stations. Although the two operating rooms 100-1 and 100-2 are shown as being identical in FIG. 1, they may have different configurations of devices. Despite the name, the client system in nurse's station 200 may be operated by any user regardless of whether or not they are a nurse. There may also be remote locations, such as a remote hospital 400 or other facility that is physically located outside of the hospital network 600 and a boardroom, training center or other room 500 where users can access audio and video feeds remotely.

Server 300 may also be connected to a hospital network 600 used within the facility for a variety of purposes, including for example, device communications, user authentication, diagnostics, and media streaming. The network communications between server 300 and other devices on hospital network 600 are preferably bi-directional communications over an IP network.

Various devices may be located in each operating room 100, such as a room light, room camera, controllable surgical table, display device (LCD, PDP), CD player, DVD recorder, VTR, and reference image storage servers. These devices are connected to server 300 and are controlled by a client system which is also connected to server 300. The connection configuration and the internal configuration of the operating room is preferably as follows.

Environmental devices 110-1 and 110-2 control illumination, temperature, humidity, air flow and other environmental conditions in operating rooms 100-1 and 100-2, respectively.

Operating rooms 100-1 and 100-2 include a respective plurality of AV devices 120-1 and 120-2. Any device that has audio and/or video inputs or outputs is considered an AV device. These AV devices may include one or more cameras, which may monitor portions of the operating room, such as an operating table, recorders, printers, audio microphones and amplifiers, speakers, etc. Although the AV devices are generally described as being controllable through the control system, any particular AV device need not be controllable through the control system. One or more of the medical devices 130-1 and 130-2 may provide a video signal or image signal to server 300 as well. Thus, some medical devices will also be considered an AV device.

The server 300 is a computer with enhanced input/output of data and can play the received audio and video signals on one or more client systems 140. Each client system 140 is a computer with a human user interface that allows the user to operate the control system. Preferably, the computer has a touch screen with a graphical user interface. Multiple client systems can be used to access central server 300 and have control of any device within the specified area or existing network that is controllable by server 300. The client/server communications between server 300 and client systems 140 are bi-directional communications over an IP network. As shown, one of ordinary skill in the art will see that the medical environment control system comprises a plurality of client systems 140 that are each located at different locations. One having ordinary skill in the art will also see that the server connects to each Audio/video device 120 and each client system 140 through its own individual network connection. The server may connect to an audio/video device 120 over a different network connection than a client system 140.

Server 300 also includes and/or has associated therewith one or more storage devices (not shown) to store the received audio, image and video signals. There may also be a printer controlled by the server 300 to print out images or other information. The server 300 is controlled by one of the client systems to perform communication of the data such as image files as to other operating rooms or conference rooms within the hospital, or to store the data from the acquired image files and so forth.

The AV devices may include a display device such as an LCD or PDP, a room light, room camera, ceiling camera, image storage device, peripheral apparatus such as a DVD recorder or CD player or printer, a video-conferencing system, and an ordering device. The image storage device may stores patient image files. These AV devices are controlled by being connected to the server 300. The server 300 is connected to client systems 140, which can be operated through a touch panel graphical user interface (GUI) to set and control the AV devices as desired. The client system can control the devices in any number of ways, such as by turning them on or off. For a light, the client system can increase or decrease the illumination, etc.

The server 300 has internal, external or removable memory (not shown) which stores the data relating to the connected AV devices, control commands, setting values, and so forth. The server 300 may also store a plurality of default settings that may be used to control the devices respectively for a particular surgeon, medical personnel, procedure or other preference. When one of the default settings is selected at a client system, the selection is transmitted to the server 300. The server 300 initiates the default setting, selects the affected devices, and sets the desired control commands and setting values for the affected devices. Thus, the operating room 100-1 or 100-2 can be easily prepared and automatically set for a particular surgeon, medical personnel, procedure or other preference at any one of the client systems. In addition to audio/video signals from AV devices, the server 300 can preferably receive control commands from at least some of the devices when control, buttons or switches on the devices are operated.

Figure 2:
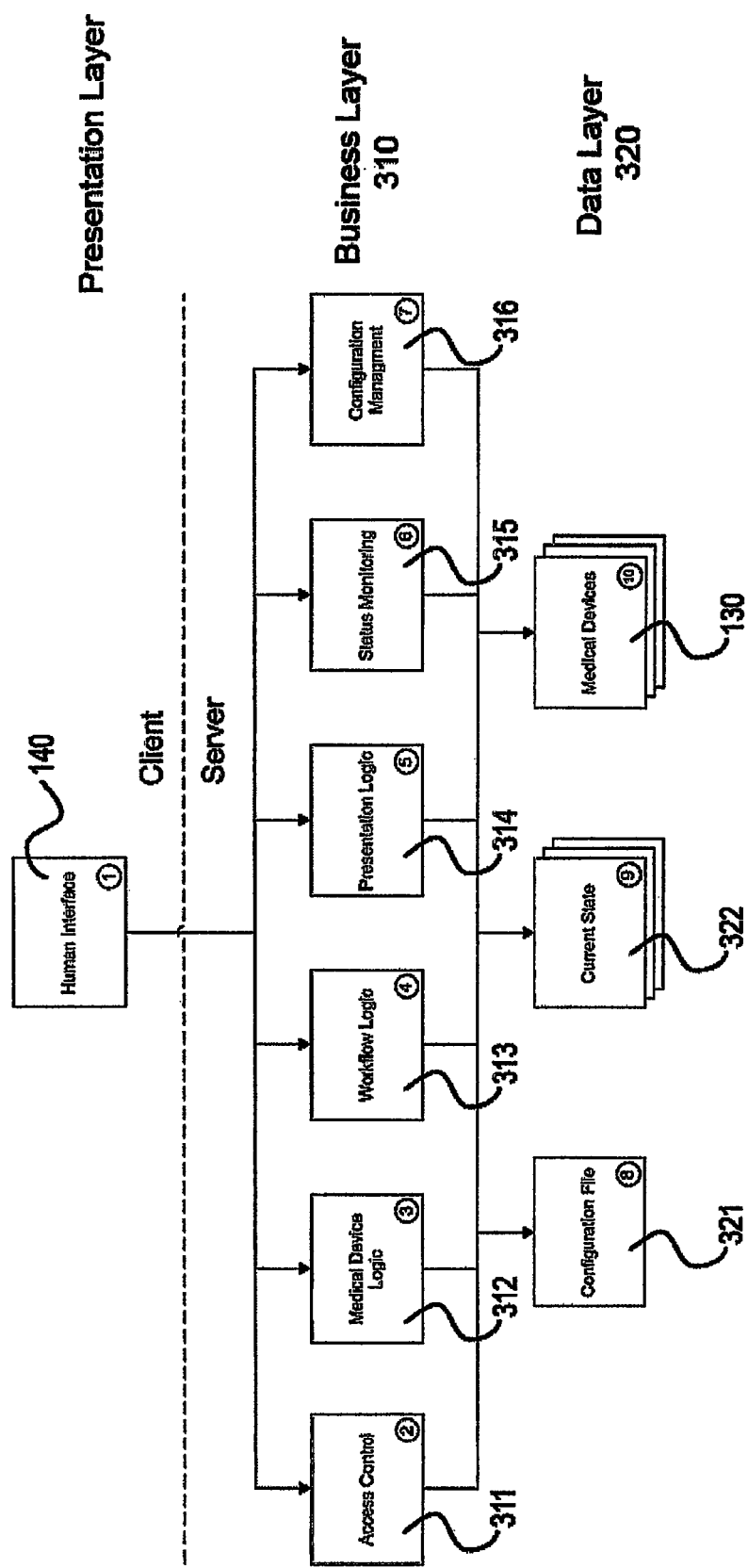
FIG. 2 is a diagram of a preferred distributed client server model which may be utilized in the preferred embodiment of the invention shown in FIG. 1.

FIG. 2 illustrates a preferred distributed client server model for the preferred embodiment shown in FIG. 1. The client side of the model consists of client systems 140. The presentation layer of client systems 140 includes a human user interface that presents information to a user and allows the user to operate the control system. In a preferred implementation, the interface is a touch screen GUI and is created using Windows forms controls and custom graphics to make the controls unique and much more pleasing to work with. The GUI only shows controls that a user should be able to work with (i.e. only shows connected devices and only shows functionality of those devices). Additionally, the presentation layer of a client system 140 sends commands to server 300 for what the user is requesting to do. As a result, the client system 140 receives a message or messages to update the entire current state of the screen they are at, regardless of whether or not their request was completed successfully or not. The GUI visually shows if buttons are pressed, options are enabled/disabled, and if items are selected so that the interface is obvious, straightforward, and intuitive.

If the client system 140 utilizes a Windows® operating system, then the preferred software components for the presentation layer include Windows form controls, sockets/network communications and a touch screen driver (not shown in FIG. 2). Windows forms hosts the core user interface and allows for rich UI experience with development flexibility. There are several "User Controls" that are the basis for some custom controls that are a combination of base windows controls. These are used to create a re-usable control with features not directly found built into the standard Windows forms controls. The .NET sockets are used for communications between the GUI and server 300. The touch screen driver is a system level driver providing, for example, USB communications between the touch screen panel on the monitor and the client system 140. Other software components may also be used. In particular, Windows forms controls and .NET sockets are specific to the Windows® operating system.

The server side of the model includes a business layer 310 and a data layer 320. The business layer 310 is entirely responsible for deciding if an action can be completed, how to complete it, and then ensuring any connected client system 140 has their interface reflect this. The business layer 310 is also responsible for receiving messages from the client systems 140, validating them, attempting to process the action if it's valid, and then updating the client system(s) 140 as needed.

The business layer 310 consists of several major sections of logic, monitoring and management. Each section preferably handles errors as early as possible such that application exceptions are not propagated up to different areas of the application and logs any errors that might occur so that any bugs or otherwise undesired behavior can be easily identified by anyone examining the log.

Access control 311 provides user authentication and permissions for operation of the system to keep the control system secure. It keeps track of what client system 140 each user interface is loaded on and will bind that version of the user interface to that client system. Medical device logic 312 provides the specific command and control communication logic for each controllable device. It communicates with the medical devices 130 and ensuring there is a synchronous representation of the physical devices. The medical device logic 312 accurately reflects the control system as it is connected, the capabilities of the control system, and overrides any extra logic that is device-specific such that different devices still adhere to the expected logical flow. The medical device logic 312 handles errors that may occur in the physical devices and ensures that the control system will not be compromised because of a single minor failure for a device.

Workflow logic 313 provides the business logic that defines the operation of the control system. It consists of the high-level logic for the server application. It validates actions and handles errors at the highest level, and ensures proper communication between the client systems 140 and server 300. The workflow logic 313 also receives commands, validates that the commands are possible based on the state of the control system and then issues the command to medical device logic 312 for it to execute. The workflow logic 313 then handles the result of the executed command. Presentation logic 314 defines the graphical representation of the human interface in client systems 140. It keeps track of what the user has done on the client system 140 (i.e., selection of devices) and gathers enough information to give to the client system 140 so that it can reflect the state of the control system as accurately as possible. The presentation logic 314 remains synchronized with the presentation layer of the client system 140 so that sufficient information is provided and messages can be parsed effectively for gathering the required information.

Status monitoring 315 handles error logic, error reporting and monitors the control systems' health. It ensures any tracing or error messages are accurately noted in the control system's log. The logging process preferably ensures that any message requested to be logged is in fact written to the log, regardless of system "hiccups" or other potential errors. Configuration management 316 handles the reading and parsing of configurations as well as saving and restoring presets. It has knowledge of the control system as a whole including a collection of the devices 110, 120 and 130 and has routing abilities from a system perspective (as opposed to a deviceto-device perspective). Configuration management 316 completes actions that are not specific to device type or individual specific devices, but rather operations that are universal to all devices (i.e. establishing communications and initializing all devices).

Data access layer 320 provides IO operations and preserves persistence between application restarts. It represents all of the medical devices 130 which are controllable by server 300 and includes the basic ability to send a command and receive a response from each medical device 130. There are also more advanced IO operations such as writing to ports and sockets to communicate information to and from medical devices 130. Preferably, data access layer 320 uses the serial port and Socket objects included as part of the .Net framework.

All of the configuration information for the control system is stored in configuration files 321 in data layer 320. Preferably, configuration files 321 are in XML format, and store preset default information as well as the configuration information. Basic IO operations to read and write an XML file are provided so that the physical layout of the control system can be saved in a virtual manner. The configuration files 321 also provide the basis for how the control system behaves, so XML parsing must be error-free to ensure that the configuration files are loaded exactly as it is described in the file. Configuration management 316 in business layer 310 manages the communications and interaction with the configuration files 321.

Current state 322 includes configuration files that hold the current settings of the control system's predetermined states, stored presets and default state. Basic IO operations to read and write XML files are provided so that the current state of the devices can be stored and later retrieved. The current state of devices includes everything that can be changed via a client system 140. Users are preferably able to restart both the client system 140 and the server 300 and have the control system accurately restore itself. This also encompasses the ability to save device states to presets such that a user can restore these at a later time and have the system accurately reflect what is stored in the file.

The client system 140 or server 300 can utilize an operating system other than Windows®, such as Unix or any of its variants (Linux®, Solaris®, HP-UX®, OS-X® or Android®). Then different preferred software components will be used throughout.

In a method according to a preferred embodiment of the invention, a control system for devices in a medical environment is designed and deployed with the assistance of a graphical configuration program on a computer that is separate from the control system shown in FIG. 1. The configuration program is created by compiling code to create an executable version of the software. The compile phase generates all the components needed to run our system. All these components are then packaged into an executable installer program. The end user runs the installer program and goes through the setup. From here, all the final processes are automated. Once this is complete, the control system is ready to run.

Figure 3:
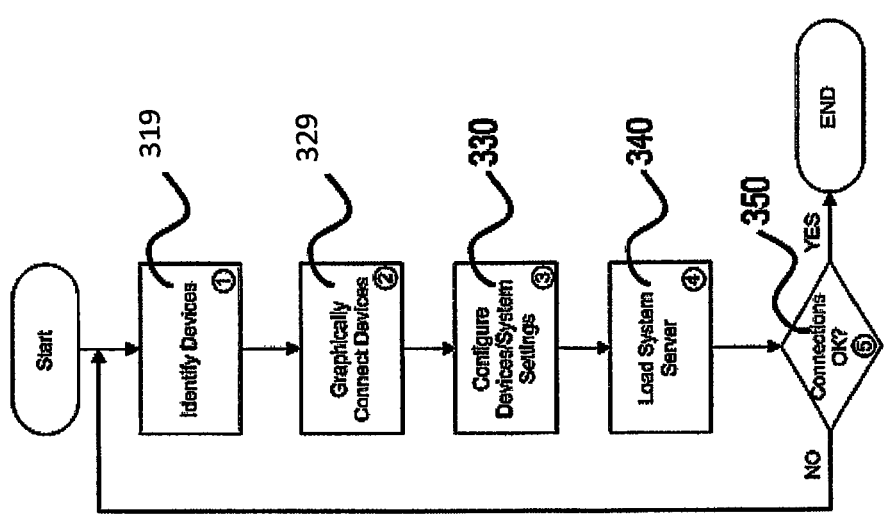
FIG. 3 is a flowchart of the creation of a control system in a surgical environment according to the preferred embodiment of the invention.

FIG. 3 is a flowchart illustrating a preferred method executed using the configuration program. The user does not need to have any special familiarity with programming language of the control system to perform the configuration. The user must only know and identify what devices will be used in the control system, how the devices will be physically connected, and any initialization parameters for each device.

In the first step 319 of the method, the user determines and identifies the devices that will be used in the control system. Preferably, this is done in a graphical configuration interface 400 such as that shown in FIG. 4 by dragging and dropping the required devices from a device list 401 having all of the devices available to the user, into a design area 402. The device list 401 preferably can be controlled to display all known devices or to only display devices of a specific type. Each device can be displayed with its default icon as well as a basic description of the device. The design area 402 preferably lets users move around existing devices.

In the next step 329, the user creates graphical interconnections of audio, video and control pathways within the design area 402 to represent a virtual connection. From the design area the user makes connections by selecting the source port (e.g., camera video out) and then the destination port (e.g., switch video in). These virtual connections are saved to a configuration file 321.

Figure 4:
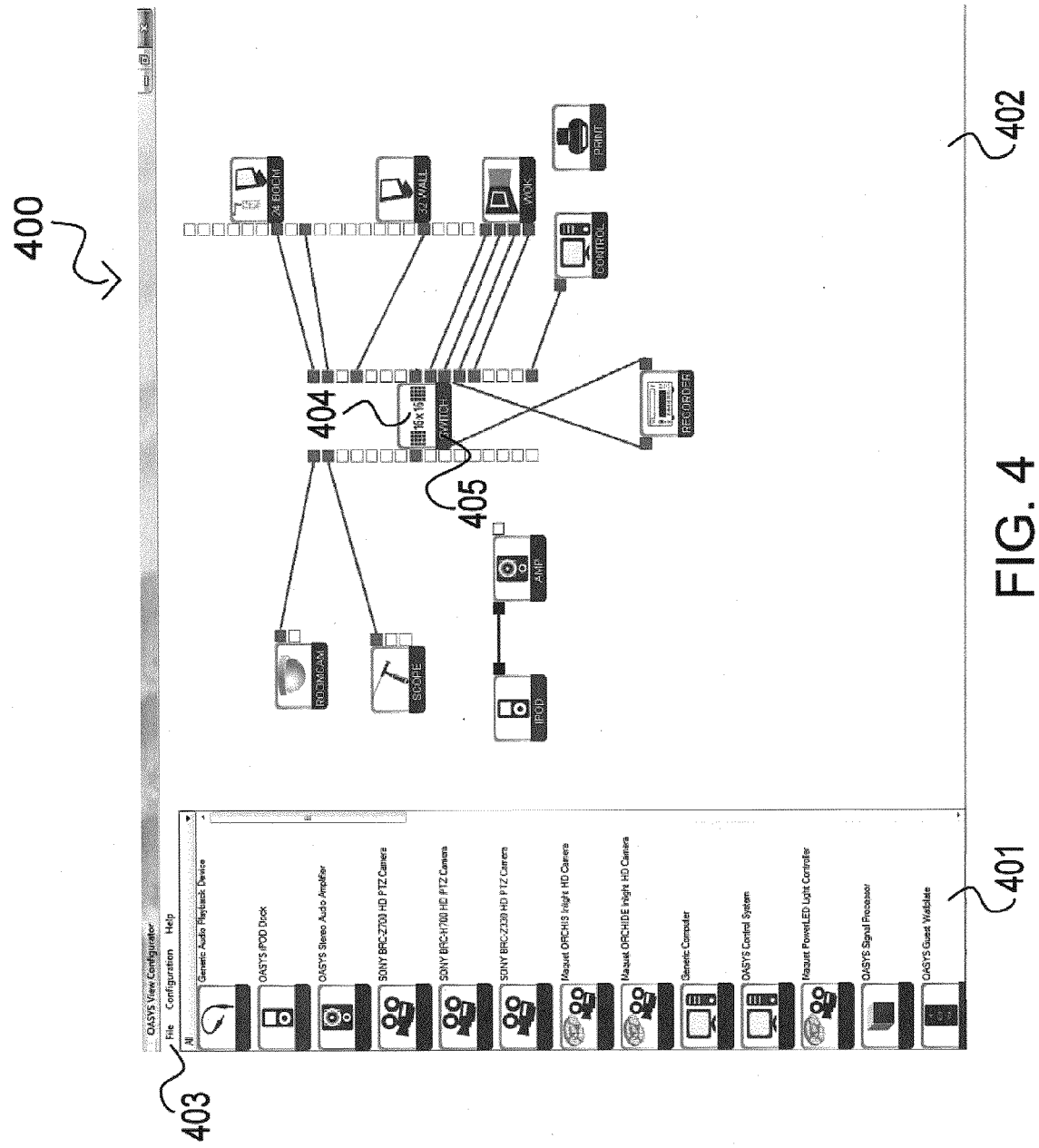
FIG. 4 is a graphical configuration interface for configuring the devices in a control system according to a preferred embodiment of the invention.

FIG. 4 shows an example of a graphical configuration interface 400 having a layout for a 16×16 switch device. There is an icon 404 and an icon tag 405 for the device which can be changed when modifying the device's properties. The device's icon tag is the text ("Switch") that will be shown by a client system 140 in actual use.

The squares on the left hand side of the icon 404 define the inputs of the device. The square on the right hand side of the icon 404 define the outputs of the device. Solid squares indicate a completed connection while unfilled squares indicate no connection. A device can have both audio and video outputs. Preferably, squares are made one color to represent video inputs and outputs and a different color to represent audio inputs and outputs. Preferably, information about a connection is displayed by hovering a cursor over a connected or disconnected input or output.

Figure 5:
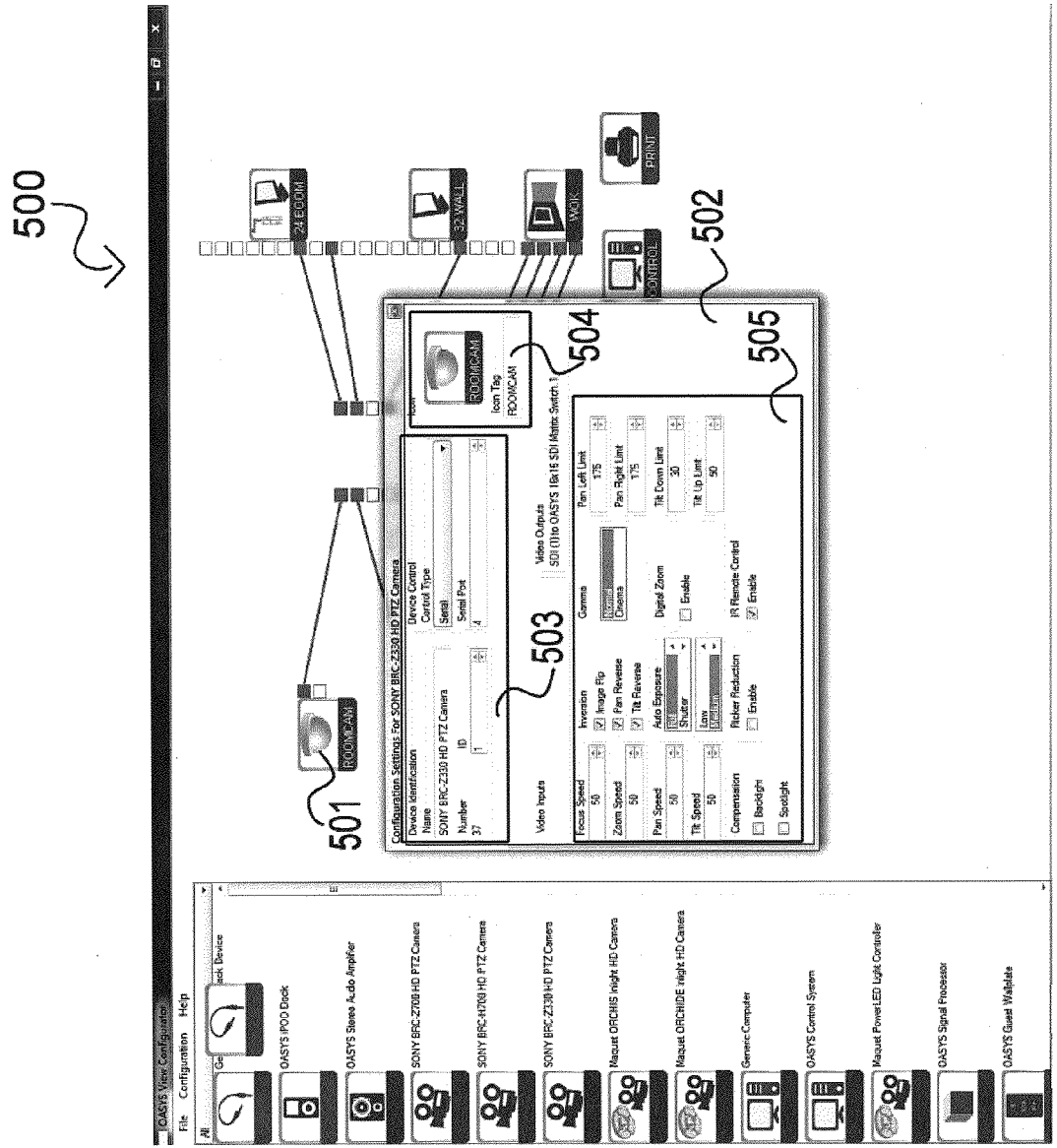
FIG. 5 illustrates a preferred window 500 for setting device specific parameters according to a preferred embodiment of the invention, as shown in FIG. 4.

FIG. 5 shows a preferred window 500 for setting device specific parameters. The parameters can be set by double clicking on the icon 501. A pop-up window 502 appears that allows the user to adjust run time and default parameters for the device. The communication parameters are preferably set in area 503. The device icon as displayed on the client system 140 can be selected from a pre-defined database of icons and the device name can be set in area 504. Parameters that are initialized at run time are set in area 505. Preferably, parameters will enable the user to configure many features of the device specific to the target deployment. For example, parameters for a camera may include, pan speed, tilt speed, pan left limit, pan right limit and digital zoom enable.

Referring back to FIG. 3 at step 330, the user then configures individual devices and makes system settings. The user sets the initialization parameters of each device, preferably by double clicking the device icon on the graphical user interface. Various parameters such as icon type, icon name, and control type, etc. can be set. Once completed, the user saves the settings in a configuration file, which is preferably an xml (extended markup language) file. If for any reason, the user wants to make changes after the initial setup, they can reopen and modify the existing configuration. Preferably, the graphical configuration interface 400 includes a menu strip 403 that provides easy access to functions such as saving and loading configurations, and making settings for the current configuration.

Figure 6:
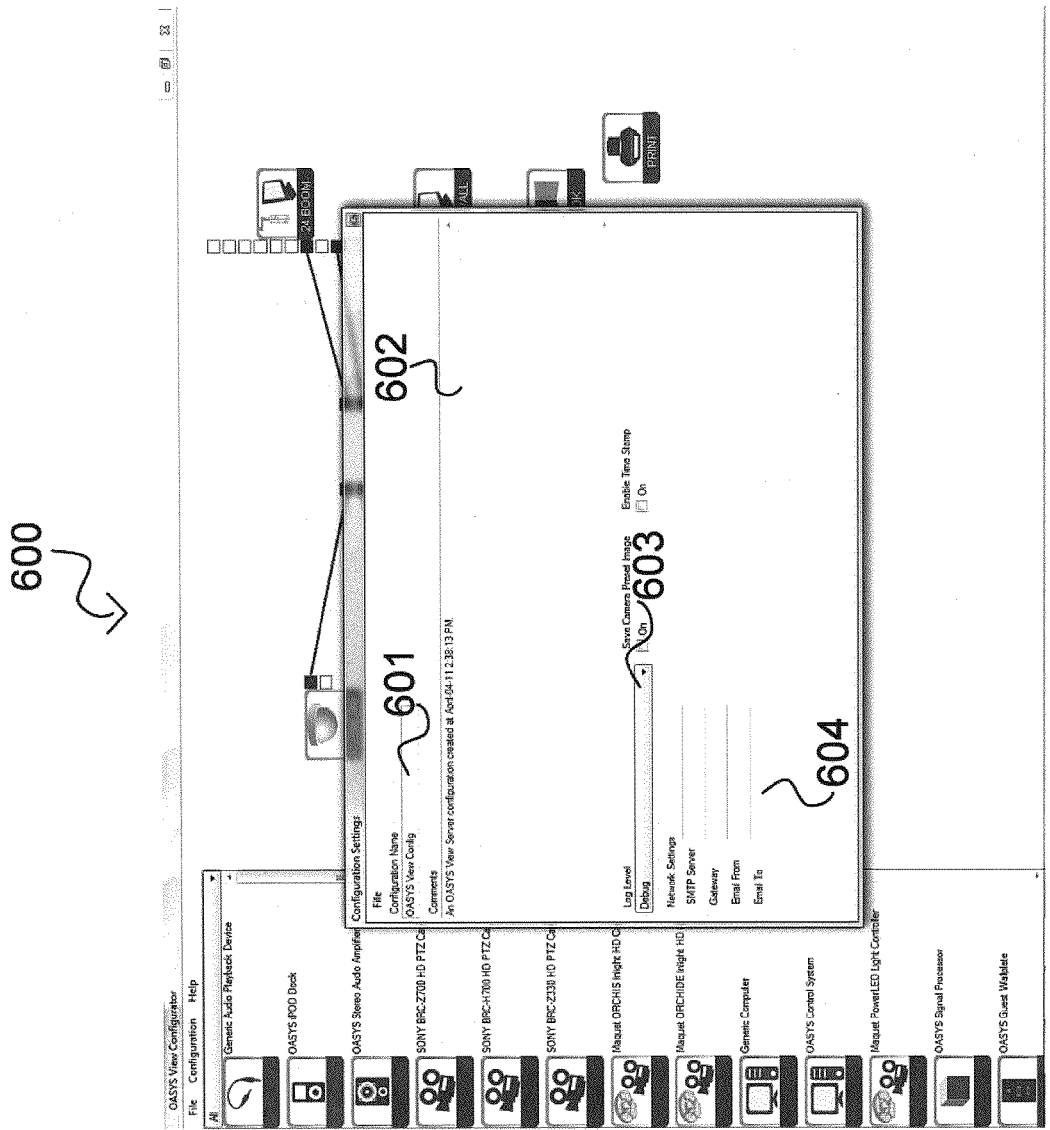
FIG. 6 illustrates a window for making configuration wide settings in the graphical configuration interface shown in FIG. 4.

FIG. 6 shows a window 600 for making configuration wide settings accessible from the configuration drop down menu in menu strip 403. The desired name of a configuration can be inputted at field 601 and comments can be inputted in section 602. The level of detail at which the server 300 logs information can be set by selecting a level from the dropdown menu 603. The available levels preferably include: 1) Debug (for developers); 2) Comm (for messages sent and received from server 300); 3) Trace (for messages that identify when server 300 is processing); 4) Info (for event messages); and 5) Error (for only errors). Email settings can be made in area 604 to designate email addresses, which can be used, for example, to permit the log or other diagnostic information to be emailed to a desired address. Such an interface 400 allows an ordinary user without any specialized programming knowledge to design the control system without doing any programming.

At step 340, the user transfers the settings configuration file and loads it to a predefined directory on the server 300 of the control system. When the control system is turned on and powers up, it runs a control application, which reads the configuration file and dynamically generates a custom user interface on client systems 140. The end user preferably uses a touch screen monitor to access this user interface and control devices in the control system. At step 350, it is checked to make sure that all the connections in the configuration are correct, i.e. the actual physical connections between each of the audio/video devices and each of the client systems. If they are correct, then the process ends. If the connections are not correct, then the method starts back at the beginning of creating the configuration in step 319.

The control system enables any user to easily control and manage the devices in the medical environment from one of the client systems 140. The available functions preferably include video routing from any source device to any destination device, previewing selected sources on-screen, adjusting image settings for video sources, changing multi-picture (including but not limited to picture-in-picture, picture-by-picture, and quad-picture) capabilities on supported displays, controlling camera settings such as panning, tilting, zooming, and focusing with presets available, operating medical-grade video recorders, selecting and listening to audio, and video conference calls.

Figure 7:
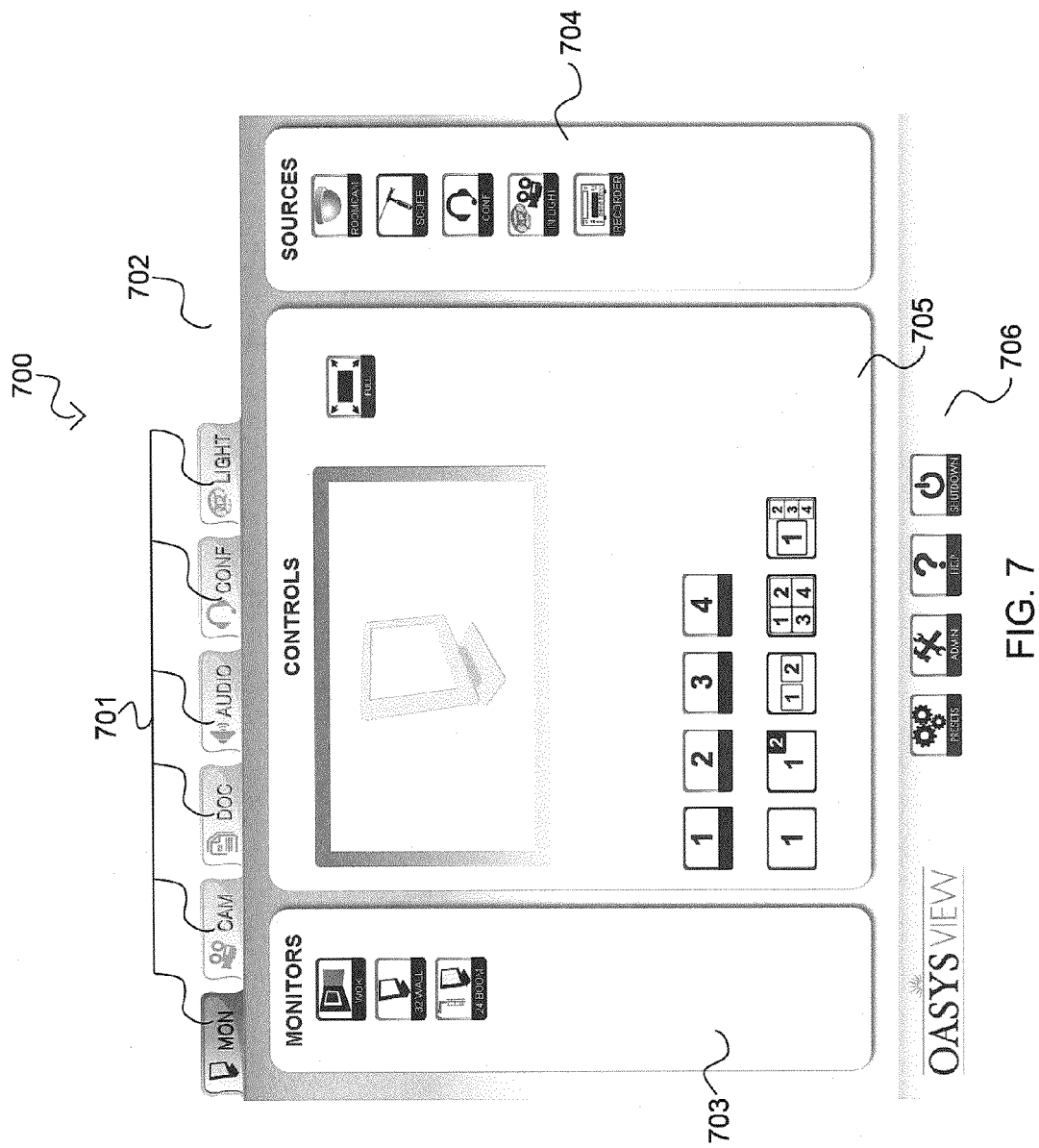
FIG. 7 is an exemplary touch screen interface for use in client systems 140 of the control shown in FIG. 1.

An exemplary and preferred touch screen interface 700 for use in client systems 140 is shown in FIG. 7. The interface includes a navigation panel 702, which may separate functionality across multiple tabs 701. The tabs preferably vary depending on the devices and capabilities of a particular configuration.

Areas 703 and 704 allow selection of devices. When routing video, area 703 defines the monitor that is the destination of the video and area 704 defines the source of the video. Functional controls are located in the center area 705. These controls allow the manipulation of selected devices in the control system. Area 706 at the bottom of the screen is a report area where system messages can be displayed.

Figure 8:
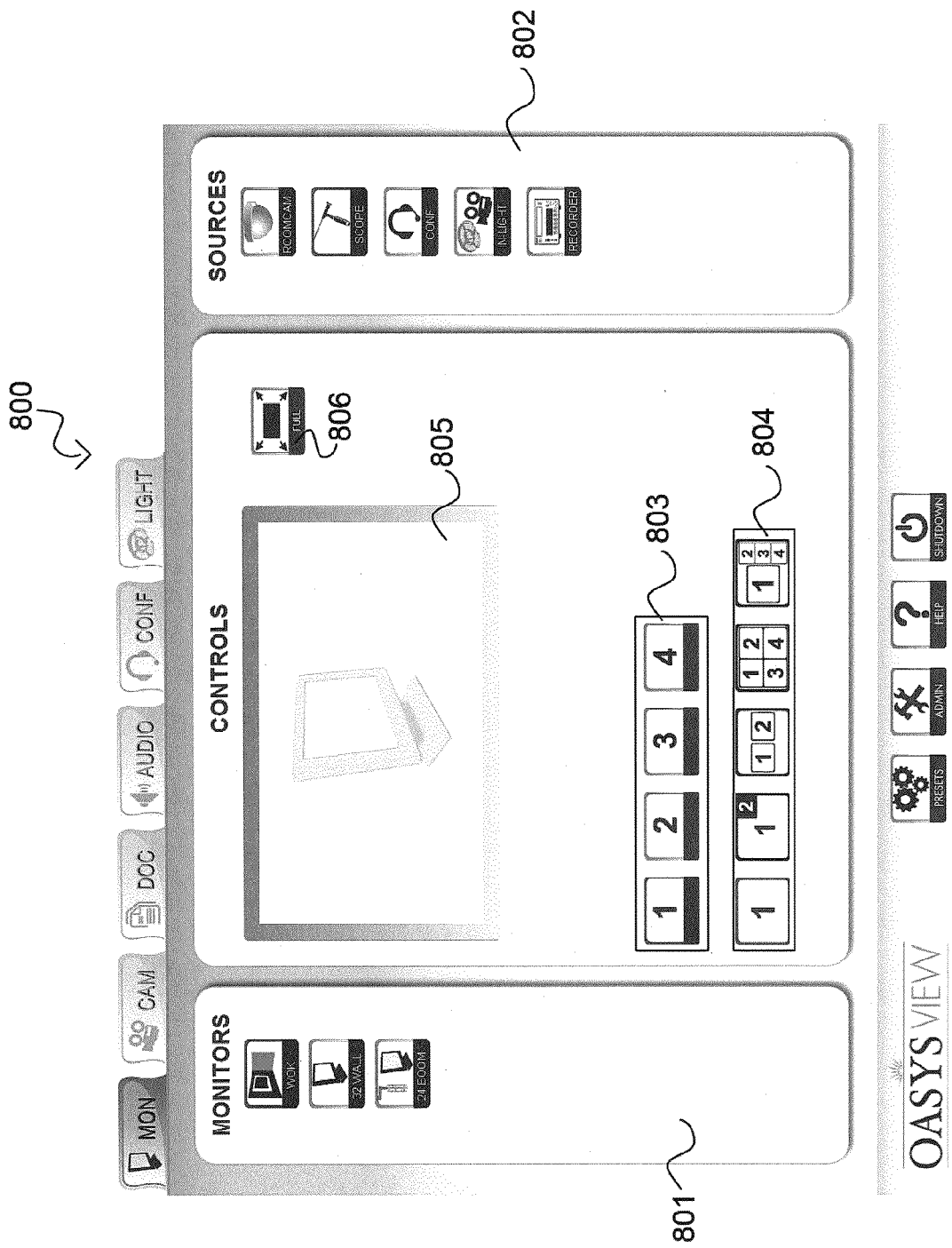
FIG. 8 shows the display when the monitors tab of the touch screen interface in FIG. 7 is selected.

FIG. 8 shows a preferred interface 800 when a monitors tab is selected. To route a video, one merely selects a monitor in device list area 801 and a video source from the list in area 802. If the selected monitor display has multi-window capabilities, the primary or secondary or tertiary video can be selected at 803 and the respective source for them chosen from area 802. There may also be selections for multi-window size and/or layout provided at 804. If enabled, the video source can be shown in panel 805, with full screen available by pressing on panel 805 or selecting the adjacent full screen button 806. The interface 800 also preferably provides a variety of video adjustments. The adjustments may include freezing, digital zooming, brightness and contrast, as well as panning of a digitally zoomed video source.

Figure 9:
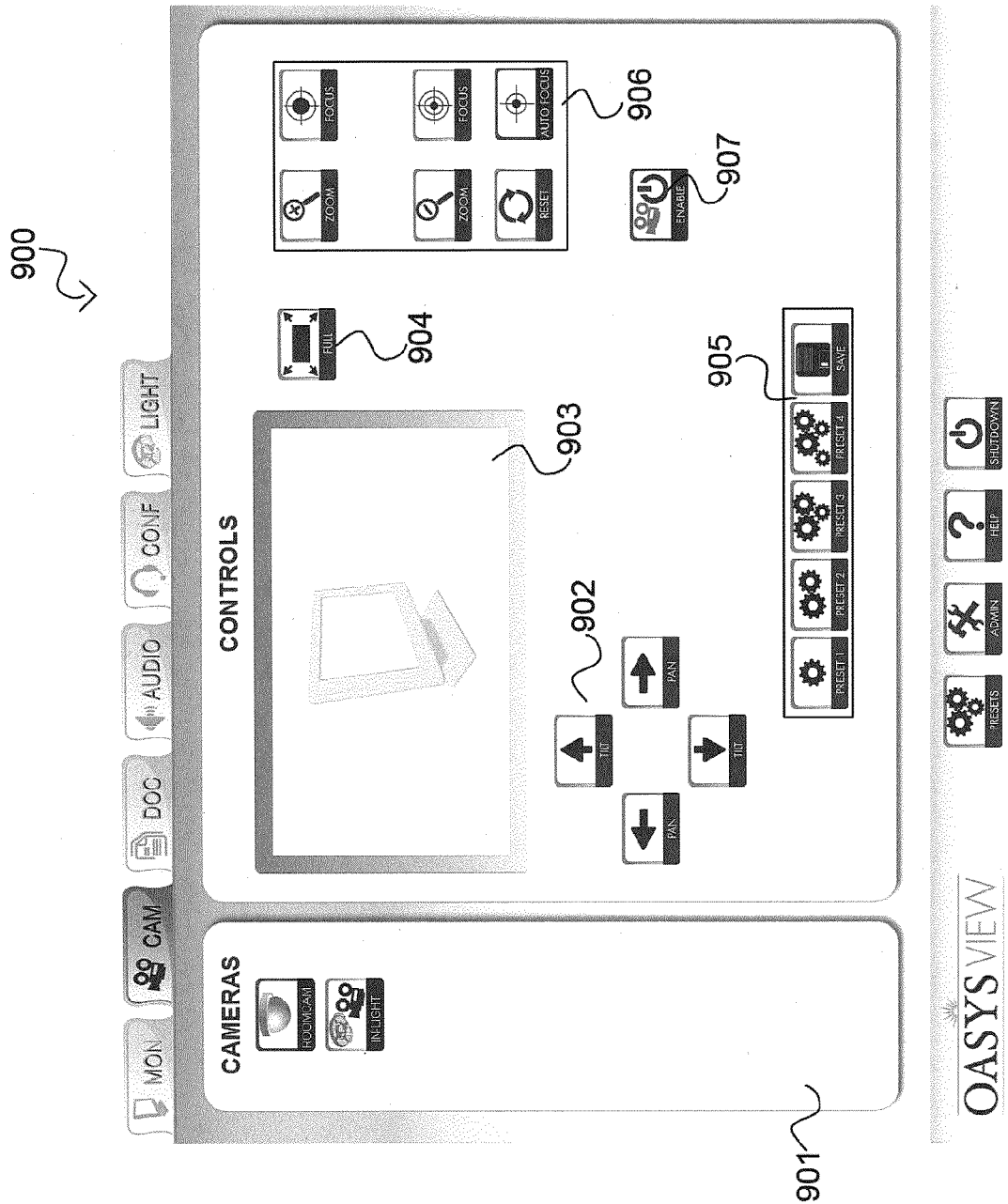
FIG. 9 shows the display when the camera tab of the touch screen interface in FIG. 7 is selected.

FIG. 9 shows a preferred interface 900 when a cameras tab is selected. A camera can be moved by selecting it in area 901, holding and releasing one of the pan/tilt buttons at 802. Video can be previewed as described with respect to FIG. 8 at panel 903 and full screen toggle button 904. In a camera preset area 905, a preset can be loaded by pressing the desired preset button. A camera preset can be saved by selecting the save button in area 805 followed by the desired preset button. Various zoom and focus controls are preferably available in area 906. The ability to transmit video can be preferably be turned on and off by toggling the enable button in area 907.

Figure 10:
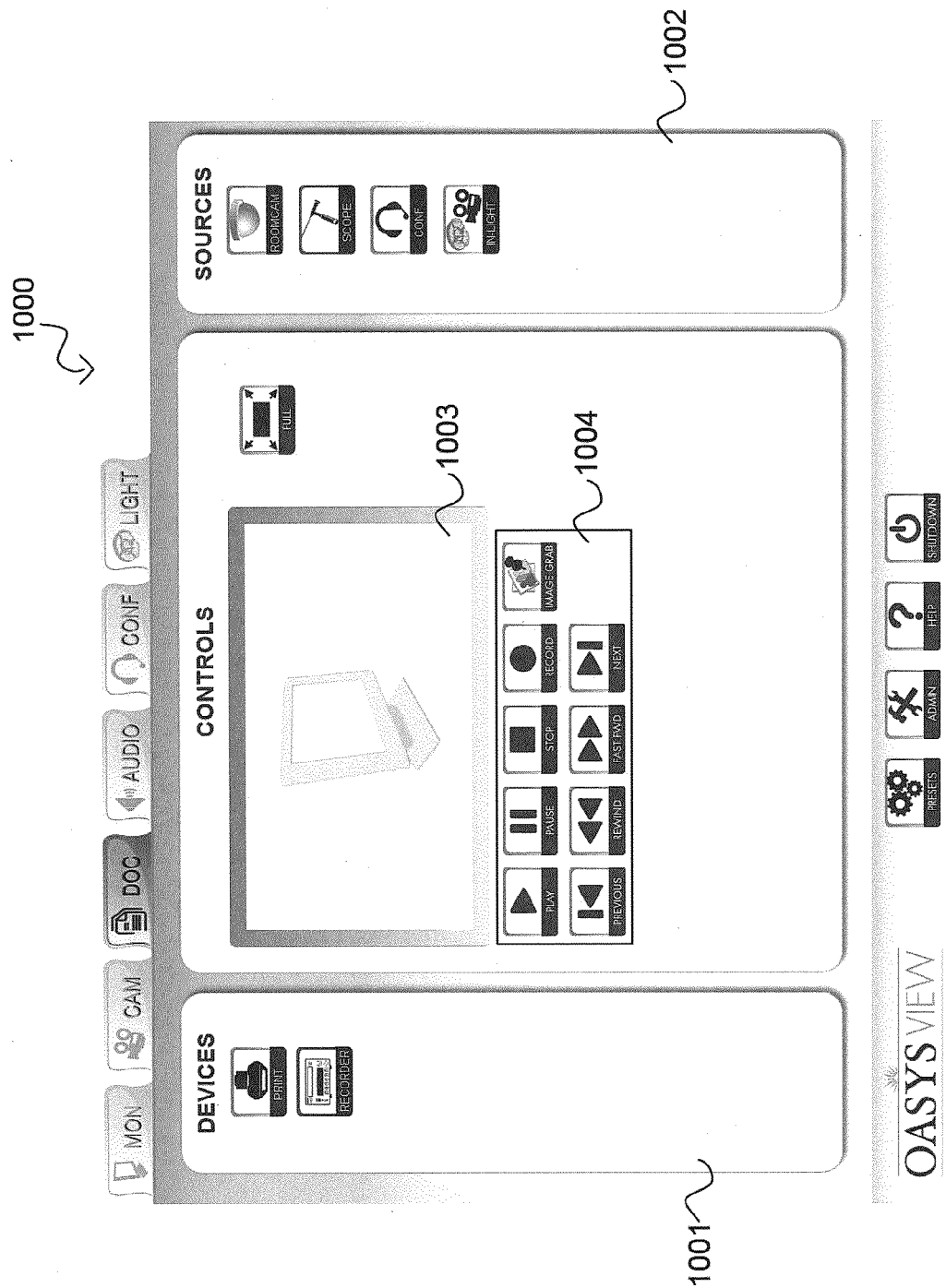
FIG. 10 shows the display when the documentation (recording) tab of the touch screen interface in FIG. 7 is selected.

FIG. 10 shows a preferred interface 1000 when the documentation tab is selected. To route video to be documented, select a recorder in left device list 1001 and select the video source from the right source list 1002. Recording and playback controls are preferably available 1004. Preferably, source preview is available at panel 1003 and full screen preview available as described above with respect to FIG. 8.

Figure 11:
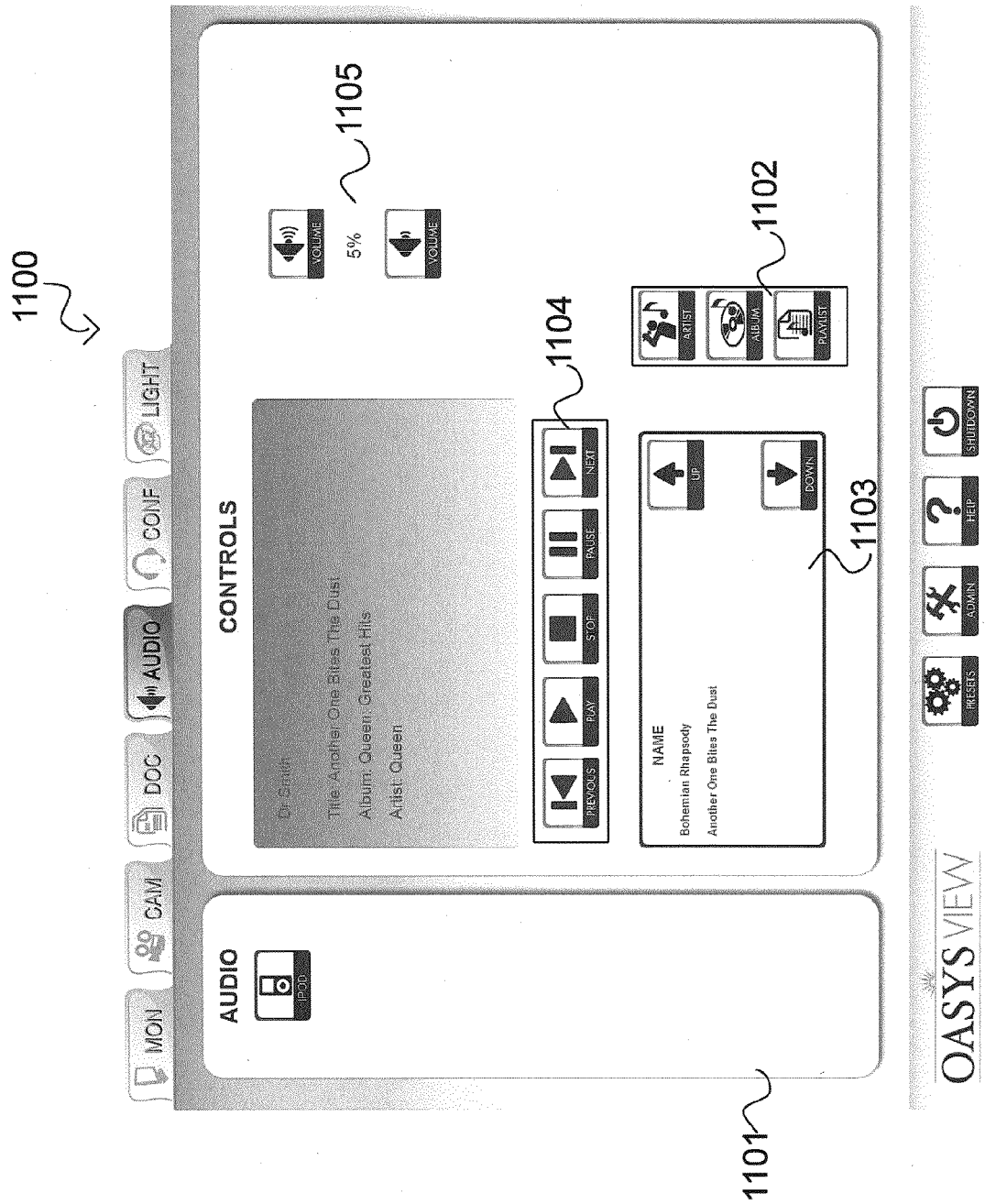
FIG. 11 shows the display when the audio tab of the touch screen interface in FIG. 7 is selected.

FIG. 11 shows a preferred interface 1100 when the audio tab is selected. To select a song, select an audio device from the left side device list 1101 and select the category, either Artist, Album or Playlist from selection area 1102. When the navigator in area 1103 is updated with entries reflecting the selection, any one of the entries can be selected. Various playback controls are preferably provided at area 1104 and volume controls 1105 are also provided.

Figure 12:
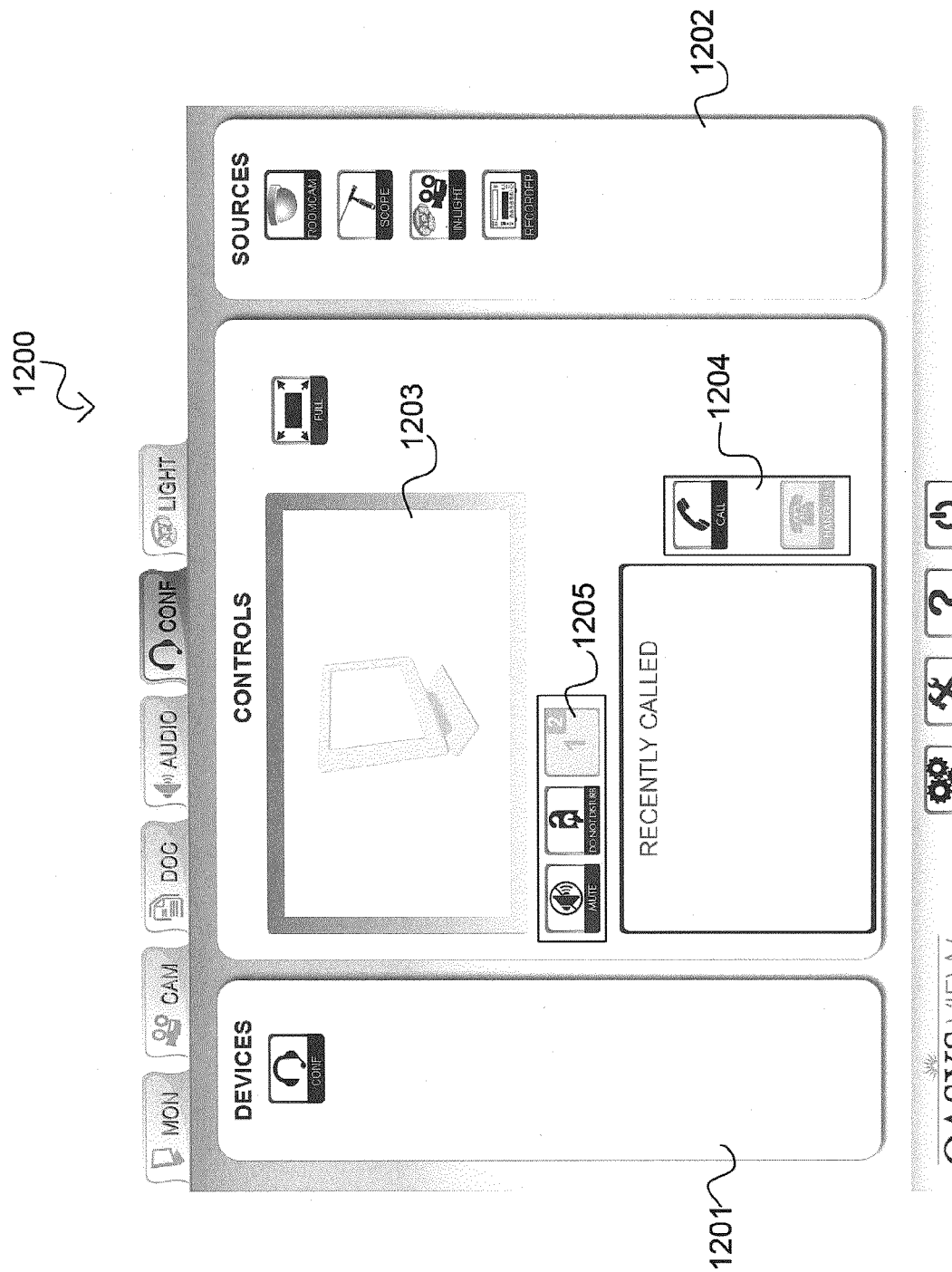
FIG. 12 shows the display when the video conferencing tab of the touch screen interface in FIG. 7 is selected.

FIG. 12 shows a preferred interface 1200 when a video conferencing tab is selected. To make a call, a video conferencing unit is selected from the left side device list 1201 and a video source is selected from right side source list 1202. A list of previous video conference session locations is preferably displayed on screen 1203. A session can be initiated again to a previous session location be selecting it from the list. Alternatively, a new number can be called by selecting the call and hang up buttons 1204. Various controls 1205 for a video conference call, such as mute, do not disturb or view selection, are preferably provided as well. Preferably, source preview is available at panel 1206 and full screen preview available as described above with respect to FIG. 8.

Figure 13:
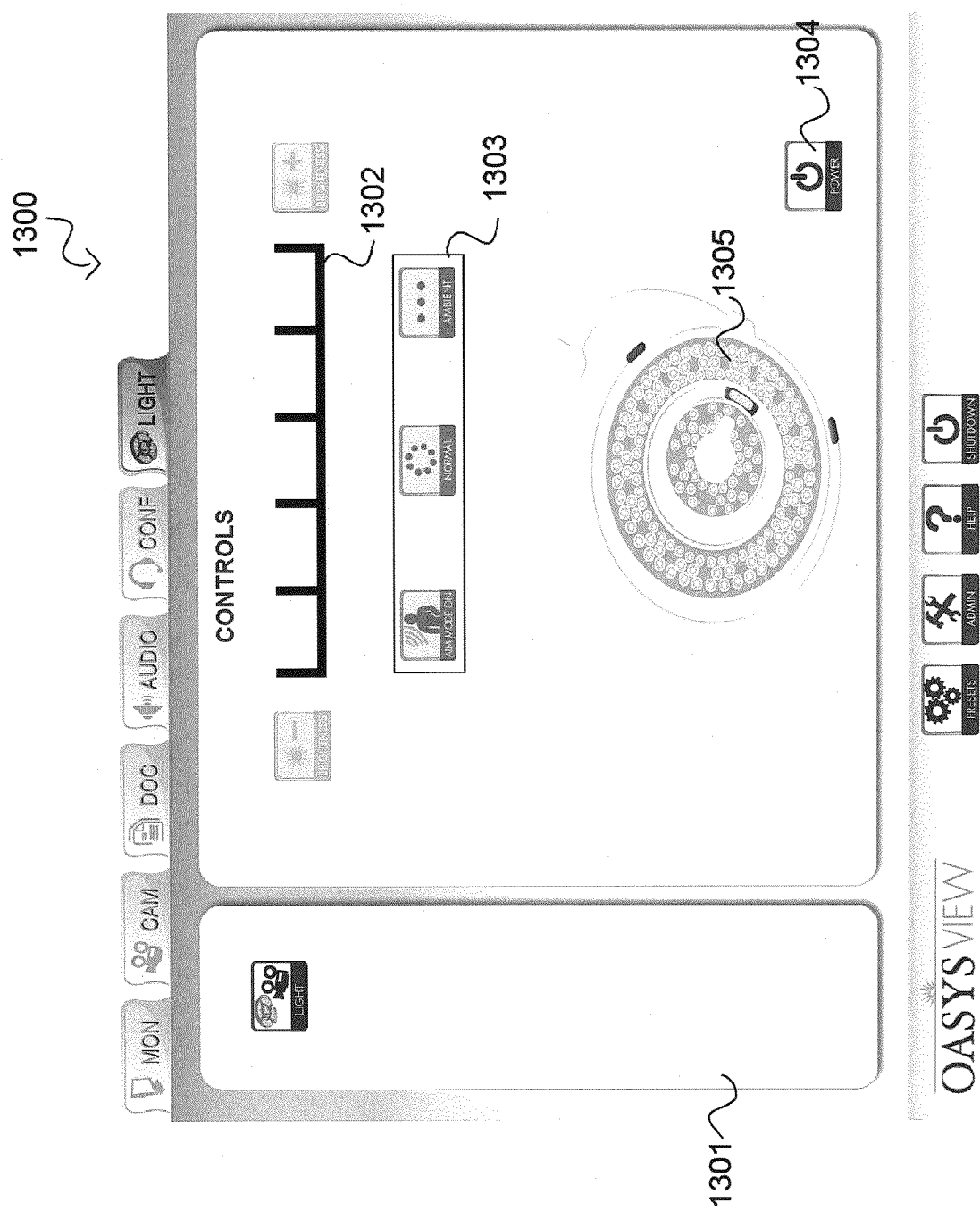
FIG. 13 shows the display when the lighting tab of the touch screen interface in FIG. 7 is selected.

FIG. 13 shows a preferred interface 1300 when a light control tab is selected. To select a light, select a device from the left side device list 1301. The brightness of the light is preferably controlled at area 1302. The mode of the light is preferably controlled at area 1303. The selected light can preferably be toggled on and off at button 1304. A graphical representation of the current status of the light is preferably displayed at area 1305.

Figure 14:
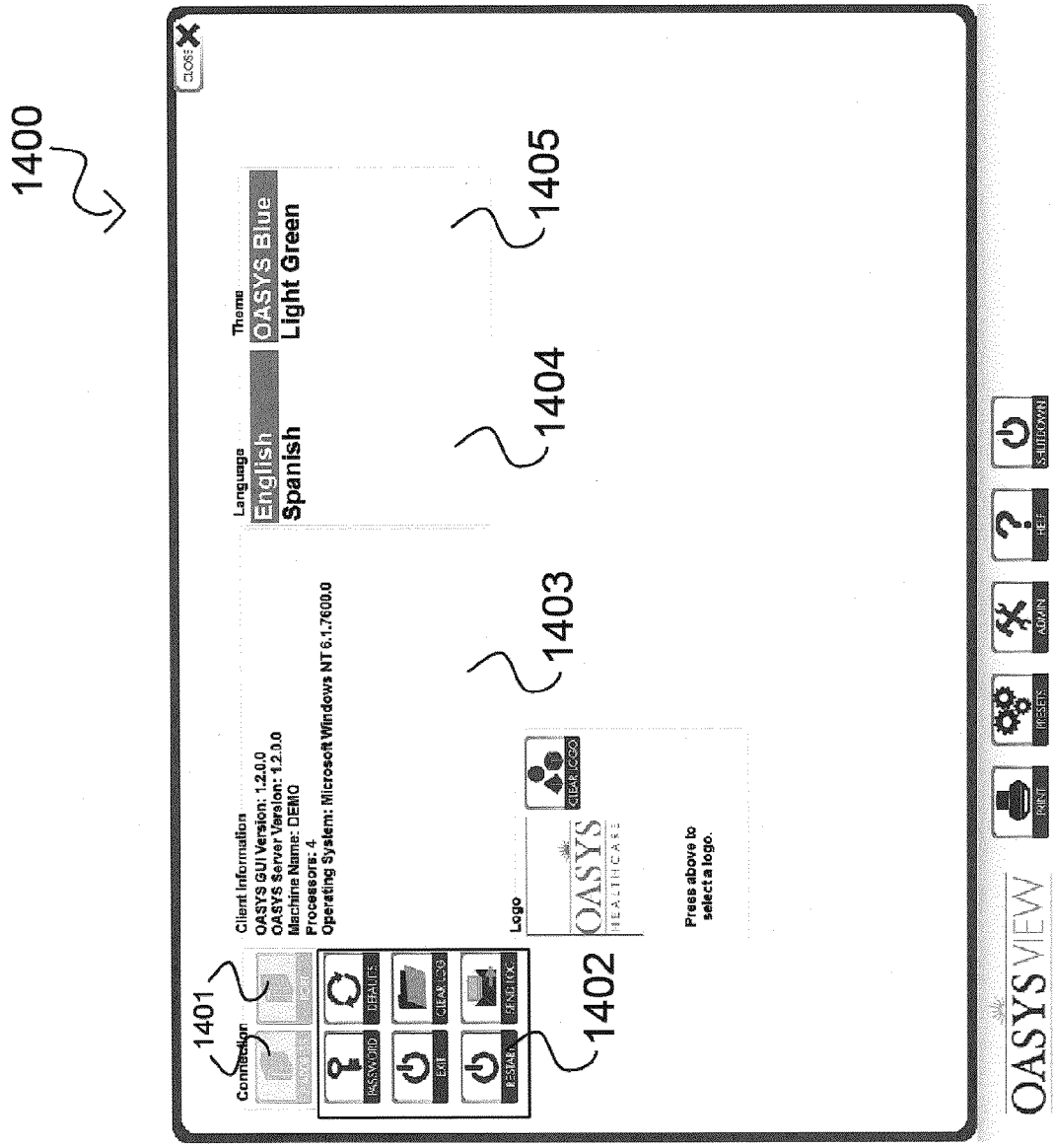
FIG. 14 shows an administrative screen of the touch screen interface of FIG. 7.

Finally, FIG. 14 shows a preferred interface 1400 which is displayed for handling administrative functions when an Admin button is pressed and a password entered. The port and IP address for server 300 can be changed by selecting buttons 1401. The password can be changed, default settings can be restored, the log file can be cleared, and the application can be exited by appropriately selecting buttons 1402. Buttons 1402 also preferably permit remote diagnostic capabilities, including transmission of system log and system configuration information, over email or other communication systems. Information regarding the current software version on the control system is displayed in area 1403. The language and theme of the application can be changed at areas 1404 and 1405, respectively.

This invention has been described and illustrated with reference to several preferred embodiments. However, the preferred embodiments are not limited to medical environments and may be used with, for example, educational, industrial or judicial environments. While the foregoing preferred embodiments of the invention have been described and illustrated in some detail for purposes of clarity and understanding, it will be appreciated by one skilled in the art, from a reading of the disclosure that various changes in form and detail can be made upon reading and understanding the preceding specification and the drawings without departing from the scope of the invention. It is intended that the invention be construed as including all such changes insofar as they come within the scope of the appended claims or the equivalents of these claims.

What is claimed is:

1. A medical environment control system comprising:
a plurality of audio/video devices that are inputs, each input is configured to receive an audio/video signal;
a plurality of audio/video devices that are outputs, each output is configured to send an audio/video signal;
a server interoperable with each input and each output, said server configured to receive audio/video signals from each output, said server configured to send audio/video signals to each input, said server comprising a data access layer that comprises configuration files;
a client system interoperable with said server and said client system interoperable with a user through a user interface in a graphical configuration program;
providing an interface having a device list area and a design area;
configuring said client system by receiving user input dragging audio/video devices from the device list area and dropping the audio/video devices into the design area;
said client system identifies the availability of each input and each output through said server;
said client system determines which output is connected to which input through said server;
said user interface displays all available inputs;
receiving a selection of one input from said available inputs;
based on the selected input, said user interface displays all connected outputs to said selected input;
receiving a selection of one said connected output;
said user interface instructs said client system to route the audio/video signal from said selected output to said selected input through said server;
displaying information about a routed connection upon receiving a hovering user input over an input or output;
said client system receives, for each audio/video signal, a user-selected input and a user-selected output;
said client system receives, in response to each audio/video device being selected as an input and each audio/video device being selected as an output, device configuration selections and system settings selections;
said server saves, to one of said configuration files, all selected inputs, all selected outputs, and all user-specified device configurations;
said server compiles code to generate an executable setup program that maps all audio/video devices that are inputs and audio/video devices that are outputs and incorporates all selected user-inputs and all user-selected outputs;
said client receives user input to run said executable setup program to generate a control application, said control application being different from said graphical configuration program; and
said control application reads said configuration file, wherein if all said connections in said configuration file are correct, said control application dynamically generates a custom user interface on said client system based on all selected inputs, all selected outputs, and all user-specified device configurations, otherwise said server reinitializes identification of each input and each output through said server.

2. The medical environment control system according to claim 1 wherein said server communicates with at least one of the over a different network connection than it communicates with said at least one client system.

3. The medical environment control system according to claim 1 wherein said client system comprises a plurality of client systems and each of said plurality of client systems is at a different location.

4. The medical environment control system according to claim 1 wherein:
said server comprises a business layer and a data access layer;
said data access layer includes configuration files; and
said business layer includes configuration management of said configuration files.

5. The medical environment control system of claim 1 wherein said user interface allows the user to control said selected input from said selected output by displaying a plurality of selectable input tabs, each input tab corresponding to a type of input;
after receiving a user selection of an input tab, displaying selectable inputs corresponding to said selected input tab;
displaying all corresponding available outputs in relation to the selected input, wherein said corresponding available outputs depend upon the input selected and are immediately selectable on the same interface screen once an input has been selected;
receiving a selection of one of said identified available inputs;
displaying all corresponding available outputs in relation to the selected input, wherein said corresponding available outputs depend upon the input selected; and
displaying within said selected input tab corresponding inputs, corresponding outputs, and controls for a selected input or output or both, each being immediately selectable by a single user input.

6. The medical environment control system of claim 1 wherein:
said user interface allows the user to control said one said connected input from said one output by displaying all corresponding available outputs in relation to the selected input, wherein said corresponding available outputs depend upon the input selected and are immediately selectable on the same interface screen once an input has been selected, the user selection being accomplished through one of a point and click, double click, drag and drop, or touch.

7. The medical environment control system of claim 1 wherein said user interface permits the user to instruct said client system to route the audio/video signal from said one output to said selected input through said server.

8. The medical environment control system of claim 1 wherein said user interface displays all available outputs and all available inputs through a single window on said user interface.

9. The medical environment control system of claim 1 wherein said client system comprises a graphical configuration interface for allowing the user to instruct said client system which inputs and outputs are connected together.

10. The medical environment control system of claim 1 wherein:
said client system comprises a plurality of client systems;
each of said plurality of client systems is located in different locations; and
each of said plurality of client systems is interoperable with each output and each input through said server.

11. The medical environment according to claim 1, wherein the relation of a selected input to all corresponding outputs is a one-to-many relationship.

12. The medical environment control system according to claim 1, wherein the device configuration options comprise previewing selected sources on-screen, adjusting image settings for video sources, changing multi-picture capabilities that comprise picture-in-picture, picture-by-picture, and quad-picture, controlling camera settings comprising panning, tilting, zooming, and focusing with available presets, operating medical-grade video recorders, selecting and listening to audio, and video conference calls.

13. The medical environment control system according to claim 1, wherein the user loads the settings configuration file into a predefined directory on the server.

14. A method of selecting an audio/video device from a network of connected audio/video devices for a client system in a medical environment control system comprising:
   configuring a plurality of audio/video devices as inputs wherein each input is configured to each receive an audio/video signal;
   configuring a plurality of audio/video devices as outputs wherein each output is configured to send an audio/video signal;
   configuring a server interoperable with each input and each output, the server configured to receive audio/video signals from each output, the server configured to send audio/video signals to each input, the server comprising a data access layer that comprises configuration files;
   configuring a client system to be interoperable with the server wherein the client system is interoperable with a user through a user interface in a graphical configuration program;
   providing an interface having a device list area and a design area;
   configuring the client system by receiving user input dragging audio/video devices from the device list area and dropping the audio/video devices into the design area;
   identifying, through the client system, the availability of each input and each output through the server;
   determining, through the client system, which output is connected to which input through the server;
   displaying on the user interface all available inputs;
   receiving a selection of one input from the available inputs;
   displaying on the user interface, based on the selected input, all connected outputs to the selected input;
   receiving a selection of one the connected output;
   instructing, through the user interface, the client system to route the audio/video signal from the selected output to the selected input through the server;
   displaying information about a routed connection upon receiving a hovering user input over an input or output;
   receiving in the client system, for each audio/video signal, a user-selected input and a user-selected output;
   receiving in the client system, in response to each audio/video device being selected as an input and each audio/video device being selected as an output, device configuration selections and system settings selections;
   saving on the server, to one of the configuration files, all selected inputs, all selected outputs, and all user-specified device configurations;
   compiling in the server code to generate an executable setup program that maps all audio/video devices that are inputs and audio/video devices that are outputs and incorporates all selected user-inputs and all user-selected outputs;
   receiving in the client user input to run the executable setup program to generate a control application, the control application being different from the graphical configuration program; and
   reading the configuration file in the control application, wherein if all the connections in the configuration file are correct, the control application dynamically generates a custom user interface on the client system based on all selected inputs, all selected outputs, and all user-specified device configurations, otherwise the server reinitializes identification of each input and each output through the server.

15. The method of selecting an audio/video device from a network of connected audio/video devices of claim 14 wherein the server communicates with at least one of the over a different network connection than it communicates with the at least one client system.

16. The method of selecting an audio/video device from a network of connected audio/video devices of claim 14 wherein the client system comprises a plurality of client systems and each of the plurality of client systems is at a different location.

17. The method of selecting an audio/video device from a network of connected audio/video devices of claim 14 wherein:
   the server comprises a business layer and a data access layer;
   the data access layer includes configuration files; and
   the business layer includes configuration management of the configuration files.

18. The method of selecting an audio/video device from a network of connected audio/video devices of claim 14 wherein the user interface allows the user to control the selected input from the selected output by displaying a plurality of selectable input tabs, each input tab corresponding to a type of input;
   after receiving a user selection of an input tab, displaying selectable inputs corresponding to the selected input tab;
   displaying all corresponding available outputs in relation to the selected input, wherein the corresponding available outputs depend upon the input selected and are immediately selectable on the same interface screen once an input has been selected;
   receiving a selection of one of the identified available inputs;
   displaying all corresponding available outputs in relation to the selected input, wherein the corresponding available outputs depend upon the input selected; and
   displaying within the selected input tab corresponding inputs, corresponding outputs, and controls for a selected input or output or both, each being immediately selectable by a single user input.

19. The method of selecting an audio/video device from a network of connected audio/video devices of claim 14 wherein:
   the user interface allows the user to control the one the connected input from the one output by displaying all corresponding available outputs in relation to the selected input, wherein the corresponding available outputs depend upon the input selected and are immediately selectable on the same interface screen once an input has been selected, the user selection being accomplished through one of a point and click, double click, drag and drop, or touch.

20. The method of selecting an audio/video device from a network of connected audio/video devices of claim 14 wherein the user interface permits the user to instruct the client system to route the audio/video signal from the one output to the selected input through the server.

21. The method of selecting an audio/video device from a network of connected audio/video devices of claim 14 wherein the user interface displays all available outputs and all available inputs through a single window on the user interface.

22. The method of selecting an audio/video device from a network of connected audio/video devices of claim 14 wherein the client system comprises a graphical configuration interface for allowing the user to instruct the client system which inputs and outputs are connected together.

23. The method of selecting an audio/video device from a network of connected audio/video devices of claim 14 wherein:
- the client system comprises a plurality of client systems;
- each of the plurality of client systems is located in different locations; and
- each of the plurality of client systems is interoperable with each output and each input through the server.

24. The method of selecting an audio/video device from a network of connected audio/video devices of claim 14, wherein the relation of a selected input to all corresponding outputs is a one-to-many relationship.

25. The method of selecting an audio/video device from a network of connected audio/video devices of claim 14, wherein the device configuration options comprise previewing selected sources on-screen, adjusting image settings for video sources, changing multi-picture capabilities that comprise picture-in-picture, picture-by-picture, and quad-picture, controlling camera settings comprising panning, tilting, zooming, and focusing with available presets, operating medical-grade video recorders, selecting and listening to audio, and video conference calls.

26. The method of selecting an audio/video device from a network of connected audio/video devices of claim 14, wherein the user loads the settings configuration file into a predefined directory on the server.

* * * * *